US00PP18159P2

(12) United States Plant Patent
Bergman

(10) Patent No.: US PP18,159 P2
(45) Date of Patent: Oct. 30, 2007

(54) ***CHRYSANTHEMUM* PLANT NAMED 'DARK YOROANOKE'**

(50) Latin Name: *Chrysanthemum×morifolium*
Varietal Denomination: Dark Yoroanoke

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/454,032

(22) Filed: Jun. 15, 2006

(51) Int. Cl.
*A01H 5/00* (2006.01)

(52) U.S. Cl. ..... Plt./286

(58) Field of Classification Search ..... Plt./286
See application file for complete search history.

*Primary Examiner*—Kent Bell
(74) *Attorney, Agent, or Firm*—C. A. Whealy

(57) ABSTRACT

A new and distinct cultivar of *Chrysanthemum* plant named 'Dark Yoroanoke', characterized by its upright and uniformly mounded plant habit; freely branching and vigorous growth habit; dark green-colored foliage; uniform flowering response; early and freely flowering habit; daisy-type inflorescences with red purple-colored ray florets and bright yellow-colored disc florets; and excellent postproduction longevity.

2 Drawing Sheets

Botanical designation: *Chrysanthemum×morifolium.*
Cultivar denomination: 'Dark Yoroanoke'.

BACKGROUND OF THE INVENTION

The present invention relates to a new and distinct cultivar of *Chrysanthemum* plant, botanically known as *chrysanthemum×morifolium,* commercially grown as a potted *Chrysanthemum* and hereinafter referred to by the name 'Dark Yoroanoke'.

The objective of the breeding program is to create new potted *Chrysanthemum* cultivars that are suitable for year-round production with uniform plant growth habit, good vigor, desirable inflorescence form and floret colors, fast response time and excellent postproduction longevity.

the new *Chrysanthemum* is a naturally-occurring whole plant mutation of the *Chrysanthemum×morifolium* cultivar Yoroanoke, disclosed in U.S. Plant Pat. No. 12,906. The new *Chrysanthemum* was discovered and selected by the Inventor as a single flowering plant within a population of plants of the cultivar Yoroanoke in December, 2002, in Fort Myers, Fla. The selection of this plant was based on its uniform plant growth habit, vigor, desirable inflorescence form and floret colors, fast response time and excellent postproduction longevity.

Asexual reproduction of the new *Chrysanthemum* by vegetative tip cuttings was first conducted in Fort Myers, Fla. in March, 2003. Asexual reproduction by cuttings has shown that the unique features of this new *Chrysanthemum* are stable and reproduced true to type in successive generations.

SUMMARY OF THE INVENTION

Plants of the cultivar Dark Yoroanoke have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dark Yoroanoke'. These characteristics in combination distinguish 'Dark Yoroanoke' as a new and distinct potted *Chrysanthemum* cultivar:

1. Upright and uniformly mounded plant habit.
2. Freely branching and vigorous growth habit.
3. Dark green-colored foliage.
4. Uniform flowering response.
5. Typically grown as a center-budded or as natural spray type.
6. Early flowering habit, eight-week response time.
7. Freely flowering habit.
8. Daisy-type inflorescences with red purple-colored ray florets and bright yellow-colored disc florets.
9. Excellent postproduction longevity with plants maintaining good substance and color for about four weeks in an interior environment.

Plants of the new *Chrysanthemum* differ from plants of the parent, the cultivar Yoroanoke in the following characteristics:

1. Plants of the new *Chrysanthemum* flower slightly earlier than plants of the cultivar Yoroanoke.
2. Plants of the new *Chrysanthemum* and the cultivar Yoroanoke differ in ray floret color as plants of the cultivar Yoroanoke have lavender pink-colored ray florets.

Plants of the new *Chrysanthemum* can be compared to plants of the *Chrysanthemum* cultivar Davis, disclosed in U.S. Plant Pat. No. 7,325. In side-by-side comparisons conducted in Fort Myers, Fla., plants of the new *Chrysanthemum* differed from plants of the cultivar Davis in the following characteristics:

1. Plants of the new *Chrysanthemum* flowered about one week earlier than plants of the cultivar Davis.
2. Inflorescences of plants of the new *Chrysanthemum* had darker red purple-colored ray florets than inflorescences of plants of the cultivar Davis.

3. Disc florets of plants of the new *Chrysanthemum* did not produce pollen whereas disc florets of plants of the cultivar Davis produced pollen.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of typical flowering plants of 'Dark Yoroanoke'.

The photograph on the second sheet is a close-up view of typical inflorescences of 'Dark Yoroanoke'.

DETAILED BOTANICAL DESCRIPTION

The aforementioned photographs and following observations and measurements describe plants grown during the spring in Leamington, Ontario, Canada in a polycarbonate-covered greenhouse and under conditions and practices which approximate those generally used in commercial potted *Chrysanthemum* production. During the production of the plants, day temperatures averaged 22.5° C., night temperatures averaged 18° C. and light levels ranged from 4,000 to 6,000 foot candles. Four unrooted cuttings were directly stuck in 15 cm containers, exposed to long day/short night conditions, and pinched about two weeks later. At that time, the photoinductive short day/long night treatments were started. Plants used in the photographs and for the description were center-budded and were about two months old. In the following description, color references are made to The Royal Horticultural Society Colour Chart, 1995 Edition, except where general terms of ordinary dictionary significance are used.

Botanical classification: *Chrysanthemum×morifolium* cultivar Dark Yoroanoke.

Parentage: Naturally-occurring whole plant mutation of the *Chrysanthemum×morifolium* cultivar Yoroanoke, disclosed in U.S. Plant Pat. No. 12,906.

Propagation:

*Type.*—Terminal vegetative cuttings.

*Time to initiate roots.*—About four days at temperatures of about 21° C.

*Time to produce a rooted young plant.*—About ten days at temperatures of about 21° C.

*Root description.*—Fine to thick, fibrous; white in color.

*Rooting habit.*—Freely branching; moderately dense.

Plant description:

*Appearance.*—Herbaceous daisy-type potted *Chrysanthemum* typically grown as a center-budded or as a natural spray type. Stems upright and outwardly spreading giving a uniformly mounded appearance to the plant. Freely branching habit, about four lateral branches develop after removal of terminal apex (pinching); dense and full plant habit. Strong and vigorous growth habit.

*Plant height.*—About 29 cm.

*Plant width.*—About 42 cm.

*Lateral branches.*—Length: About 22 cm. Diameter: About 4 mm. Internode length: About 1.3 cm. Strength: Strong. Texture: Pubescent. Color: Close to 144A to 146A.

Foliage description:

*Arrangement.*—Alternate, simple.

*Length.*—About 7.2 cm.

*Width.*—About 4.5 cm.

*Apex.*—Cuspidate to mucronate.

*Base.*—Attenuate.

*Margin.*—Palmately lobed, sinuses between lateral lobes parallel to divergent.

*Texture, upper and lower surfaces.*—Fine pubescence; veins prominent on lower surface.

*Color.*—Developing and fully expanded foliage, upper surface: Close to 147A; venation, close to 147A. Developing and fully expanded foliage, lower surface: Close to 147B; venation, close to 147A.

*Petiole length.*—About 2.4 cm.

*Petiole diameter.*—About 4 mm.

*Petiole color.*—Close to 146B.

Inflorescence description:

*Appearance.*—Daisy-type inflorescence form with elongated oblong-shaped ray florets. Inflorescences borne on terminals above foliage. Disk and ray florets arranged acropetally on a capitulum. Inflorescence not fragrant. Typically grown as a center-budded or as a natural spray type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants exposed to two weeks of long day/short night conditions followed by photoinductive short day/long night conditions flower about eight weeks later.

*Postproduction longevity.*—Inflorescences maintain good color and substance for about four weeks in an interior environment.

*Quantity of inflorescences.*—Freely flowering, about eight to nine inflorescences develop per lateral stem, or about 32 to 36 inflorescences per plant.

*Inflorescence bud.*—Height: About 6 mm. Diameter: About 8 mm. Shape: Oblate. Color: Close to 146A to 147A.

*Inflorescence size.*—Diameter: About 6.5 cm. Depth (height): About 1.75 cm. Diameter of disc: About 1.5 cm. Receptacle diameter: About 6 mm.

*Ray florets.*—Shape: Elongated-oblong. Orientation: Initially upright, then about 75° to about 90° from vertical. Aspect: initially incurved, then reflexed. Length: About 3.2 cm. Width: About 1.1 cm. Corolla tube length: About 4 mm. Apex: Acute or cuspidate. Base: Attenuate; short corolla tube. Margin: Entire. Texture, upper and lower surfaces: Smooth, glabrous, satiny. Number of ray florets per inflorescence: About 24 arranged in one or two rows. Color: When opening, upper surface: close to 70A. When opening, lower surface: Close to 155D faintly underlain with close to 70A. Fully opened, upper surface: Close to 70A to 70B. Fully opened, lower surface: Close to 155D more faintly underlain with close to 70A.

*Disc florets.*—Arrangement: Massed at center of receptacle. Shape: Tubular, elongated. Apex: Five-pointed. Length: About 6 mm. Width: Apex: About 2 mm. Base: About 1 mm. Number of the florets per inflorescence: about 205. Color: Immature: Close to 145A to 154A. Mature: Apex: Close to 9A. Mid-section: Close to 145C. Base: Close to 155D.

*Phyllaries.*—Number of phyllaries per inflorescence: About 22. Length: About 4.5 mm. Width: About 2 mm. Shape: Linear. Apex: Acute. Base: Truncate. Texture, upper surface: Smooth, waxy. Texture, lower surface: Pubescent. Color, upper surface: Close to 146A. Color, lower surface: Close to 146A to 147A.

*Peduncles. Length: First peduncle: About* 4.5 cm. Fourth peduncle: About 6.6 cm. Seventh peduncle: about 8.25 cm. Diameter (first peduncle): About 2.5 mm. Angle: About 45° from vertical. Strength: Strong, flexible. Texture: Pubescent. Color: Close to 144A to 146A.

*Reproductive organs.*—Androecium: Present on disc florets only. Filament length: About 6 mm. Filament color: Close to 155D. Anther shape: Oblong. Anther color: Close to 12A. Pollen amount: None observed. Gynoecium: Present on both ray and disc florets. Pistil length: About 5 mm. Stigma shape: Bi-parted. Stigma color: Close to 12A. Style length: About 3 mm. Style color: Close to 145C. Ovary color: Close to 157A.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of about 1° C. and high temperatures of about 38° C.

It is claimed:

1. A new and distinct *Chrysanthemum* plant named 'Dark Yoroanoke' as illustrated and described.

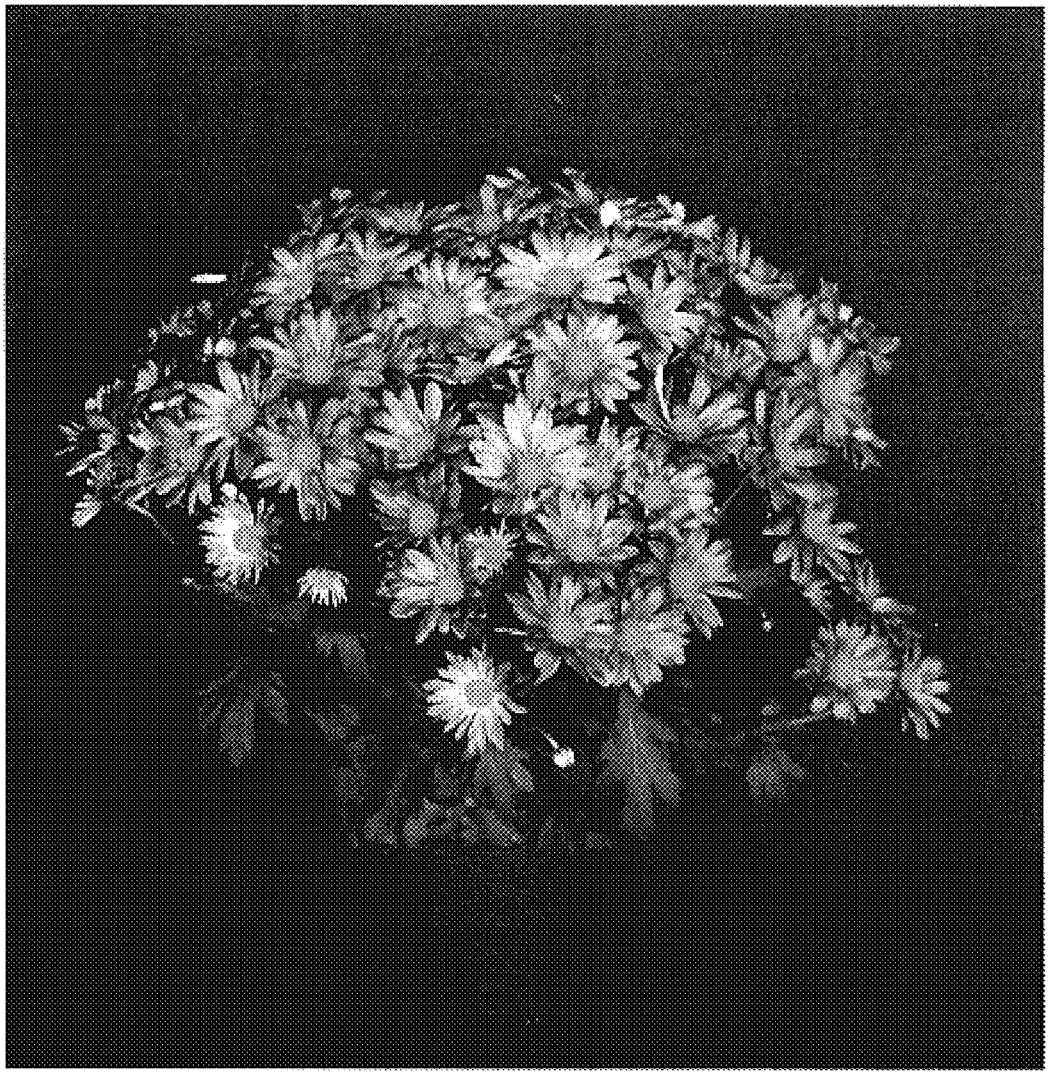

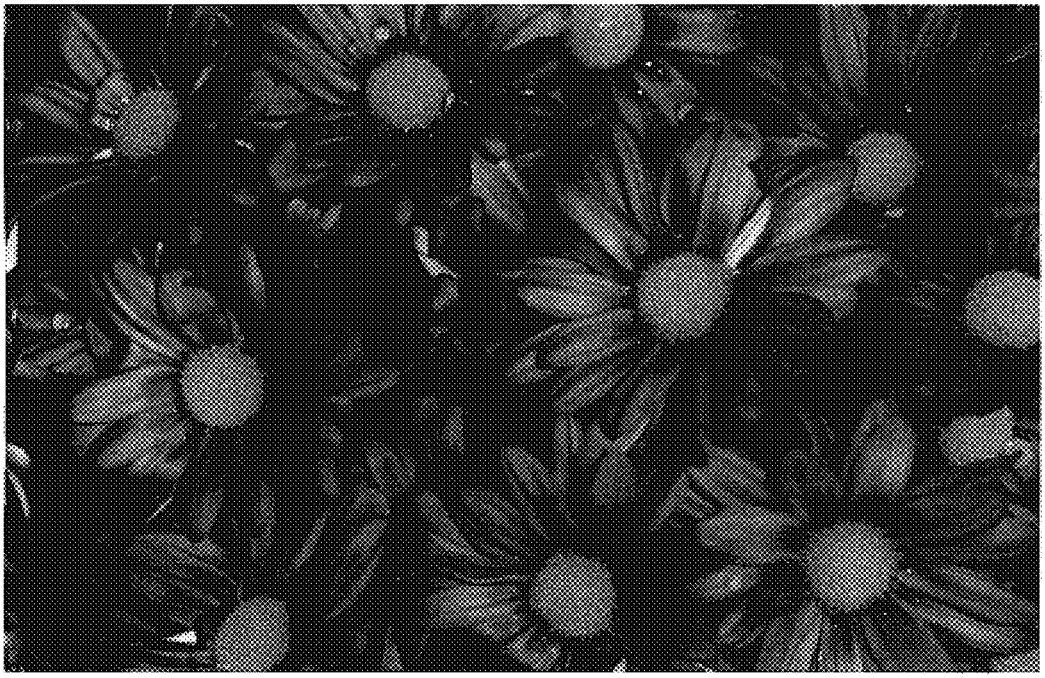

* * * * *